United States Patent [19]

Bremer et al.

[11] 4,087,446

[45] May 2, 1978

[54] PREPARATION OF MALEIC ANHYDRIDE FROM FOUR-CARBON HYDROCARBONS

[75] Inventors: Noel J. Bremer, Kent; James F. White, Akron; Ernest C. Milberger, Solon, all of Ohio

[73] Assignee: The Standard Oil Company, Cleveland, Ohio

[21] Appl. No.: 734,704

[22] Filed: Oct. 21, 1976

[51] Int. Cl.$^2$ .......................................... C07D 307/60
[52] U.S. Cl. ................................................ 260/346.75
[58] Field of Search ................................. 260/346.8 A

[56] References Cited

U.S. PATENT DOCUMENTS 3,992,419  11/1976  Otaki et al. ................... 260/346.8 A Primary Examiner—Henry R. Jiles
Assistant Examiner—Bernard Dentz
Attorney, Agent, or Firm—Gwenetta Douglas Hill; Herbert D. Knudsen; Larry W. Evans

[57] ABSTRACT

Maleic anhydride is produced by the oxidation of n-butane, n-butenes, 1,3-butadiene or mixture thereof with molecular oxygen in the vapor phase in the presence of a catalytic oxide of molybdenum, phosphorus, oxygen, and at least one element selected from the group consisting of As, Rb, Pd, Cd, Cs, Tl and In.

11 Claims, No Drawings

PREPARATION OF MALEIC ANHYDRIDE FROM FOUR-CARBON HYDROCARBONS

SUMMARY OF THE INVENTION

It has now been discovered according to the present invention in the process for the production of maleic anhydride by the oxidation of n-butane, n-butenes, 1,3-butadiene or mixture thereof, with molecular oxygen in the vapor phase at a reaction temperature of about 250° C to about 600° C in the presence of steam, the improvement which comprises using as a catalyst a catalyst described by the formula $$X_a Mo_3 P_b O_x$$

wherein
X is at least one element selected from the group consisting of As, Rb, Pd, Cd, Cs, Tl and In; and wherein
$a$ is a positive number less than about 10;
$b$ is a positive number less than about 3;
$x$ is the number of oxygens required to satisfy the valence states of the other elements present.

Especially high yields and selectivities of maleic anhydride are obtained from four-carbon hydrocarbons in an efficient, convenient, and economical manner at a relatively low temperature. The exotherm of the reaction is low, thereby allowing easy reaction control.

The most significant aspect of the present invention is the catalyst employed. The catalyst may be any of the catalysts delineated by the above formula. Preferred catalysts within the formula are described wherein $a$ is a positive number less than about 7, and catalysts wherein $b$ is a positive number less than about 2. Highly desirable results are obtained wherein $a$ is 0.01 to 3 and $b$ is 0.01 to 1.0.

Catalysts of special interest are described wherein X is at least one element selected from the group consisting of rubidium, cesium, thallium, and indium. Excellent results are obtained wherein each element delineated by X in the catalytic formula is separately incorporated into the catalyst.

The methods of preparing the catalysts of the present invention may vary widely. A number of techniques are known to those skilled in the art. Methods of catalyst preparations such as coprecipitation, evaporative drying, or oxide mixing, followed by calcining the resulting catalysts may be successfully employed.

The preferred procedure of this invention involves preparing the catalysts in an aqueous slurry or solution of compounds containing molybdenum and phosphorus, adding the remaining components; evaporating this aqueous mixture; and calcining the resulting catalysts. Suitable molybdenum compounds that may be employed in the preparation of the catalysts delineated by the above formula include molybdenum trioxide, phosphomolybdic acid, molybdic acid, ammonium heptamolybdate, and the like. Excellent results are obtained using catalysts of the invention wherein at least part of the molybdenum employed in the preparation of the catalysts is supplied in the form of molybdenum trioxide.

Suitable phosphorus compounds that may be employed in the preparation of the catalysts include orthophosphoric acid, metaphosphoric acid, triphosphoric acid, phosphorus halides or oxyhalides. The remaining components of the catalysts may be added as oxide, acetate, formate, sulfate, nitrate, carbonate, halide and oxyhalide.

The best results are obtained by refluxing phosphoric acid and molybdenum trioxide or ammonium heptamolybdate in water for about 0.5 to 3 hours, however, commercial phosphomolybdic acid may be effectively utilized; adding compounds containing elements delineated by X to the aqueous slurry and boiling to a thick paste; and drying the resulting catalysts at 110° C to 120° C in air.

By the preferred procedure of the invention, calcination of the catalysts is not generally required to obtain desired catalysts described within the above formula. However, calcination of particular catalysts of the invention may be accomplished by heating the dry catalytic components at a temperature of about 300° C to about 700° C; preferred calcination is accomplished at a temperature of 325° C to 450° C. The hydrocarbon reacted may be n-butane, n-butenes, 1,3-butadiene or mixture thereof. Preferred is the use of n-butenes, or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperature of about 250° C to about 600° C are employed with temperature of 250° C to 450° C being preferred.

The catalyst may be used alone or a support could be employed. Suitable supports include silica, alumina, Alundum, silicon carbide, boron phosphate, zirconia, and titania. The catalysts are conveniently used in a fixed-bed reactor using tablets, pellets or the like or in a fluid-bed reactor using a catalyst preferably having a particle size of less than about 300 microns. The contact time may be as low as a fraction of a second or as high as 20 seconds or more. The reaction may be conducted at atmospheric, superatmospheric or subatmospheric pressure.

Excellent results are obtained using a coated catalyst consisting essentially of an inert support material having a diameter of at least 20 microns and an outer surface and a continuous coating of said active catalyst on said inert support strongly adhering to the outer surface of said support.

By use of these coated catalysts in the reaction to produce maleic anhydride, a very low exotherm is realized allowing for better control of the reaction. High single pass yields are exhibited and the elimination of undesirable byproducts is obtained.

The special coated catalyst consists of an inner support material having an outside surface and a coating of the active catalytic material on this outside surface. These catalysts can be prepared by a number of different methods.

The support material for the catalyst forms the inner core of the catalyst. This is an essentially inert support and may have substantially any particle size although a diameter of greater than 20 microns is preferred. Especially preferred in the present invention for use in a commercial reactor are those supports which are spherical and which have a diameter of about 0.2 cm. to about 2 cm. Suitable examples of essentially inert support materials include: Alundum, silica, alumina, alumina-silica, silicon carbide, titania and zirconia. Expecially preferred among these supports are Alundum, silica, alumina and alumina-silica.

The catalysts may contain essentially any proportions of support and catalytically active material. The limits of this relationship are only set by the relative ability of the catalyst and support material to accommodate each other. Preferred catalysts contain about 10 to about 100 percent by weight of catalytically active material based on the weight of the support.

The preparation of these coated catalysts can be accomplished by various techniques. The basic method of preparing these catalysts is to partially wet the support material with a liquid. The support should not be wet on the outside surface of the total mass. It should appear to be dry to the touch. If the support is wet, then the active catalytic material may agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum and adding the active catalytic material. This is very economically done.

Using the catalysts of the invention in the preparation of maleic anhydride, excellent yields are obtained in a convenient reaction with low amounts of byproducts.

SPECIFIC EMBODIMENTS

EXAMPLES 1 to 27

Preparation of Maleic Anhydride Using Various Catalysts of the Invention

Examples 1 to 4

Various catalysts of the invention were prepared as follows:

EXAMPLE 1

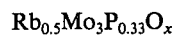

$Rb_{0.5}Mo_3P_{0.33}O_x$

An aqueous slurry was prepared by adding 55.3 grams of molybdenum trioxide to one liter of boiling distilled water with stirring; the slurry was boiled for about 2 hours. To this aqueous slurry, 4.9 grams of 85% solution phosphoric acid was added; the color of the slurry changed to yellow. About 200 mls. of distilled water was added to maintain an approximately 800 mls. solution level. To this aqueous mixture, 7.5 grams of rubidium carbonate were added; the color of the slurry became bright yellow; after about 30 minutes 25 mls. of distilled water were added. The catalyst was heated with stirring; boiled to dryness; and dried to air at about 110° C. The catalyst was ground and screened to give a 10 by 30 mesh fraction.

EXAMPLES 2 to 4

Various catalysts of the present invention were prepared. These catalysts have the general formula $X_{0.5}Mo_3P_{0.33}O_x$. The catalysts were prepared according to the procedure of Example 1, except 86.2 grams of $MoO_3$, and 7.7 grams of 85% $H_3PO_4$ were employed. The element delineated by X was added following the addition of phosphoric acid. To prepare the catalysts, the following compounds and amounts were used:

| Example | Element, X = | Compound | Amount, g. |
|---|---|---|---|
| 2 | Cs | cesium acetate | 19.2 |
| 3 | Tl | thallous acetate | 26.3 |
| 4 | In | indium acetate | 29.2 |

Following the addition of the element, X, the catalysts were boiled to dryness, dried in air, ground and screened in the same manner described in Example 1.

EXAMPLES 5 to 23

Preparation of Maleic Anhydride from Butene-2

A portion of the catalyst particles prepared in accordance with Examples 1 to 4 were charged to a 20 cc. fixed-bed reactor equipped with a 1.02 cm. inside diameter stainless steel tube.

The reactor was heated to reaction temperature under a flow of and a feed of air/butene-2/$H_2O$, as indicated below, was fed over the catalyst at an apparent contact time of 1.0 to 1.5 seconds and the performance evaluated by collecting and analyzing the products.

The results of these experiments appear in TABLE I. The following definitions are used in measuring the carbon atoms in the feed and in the product:

% Single Pass Yield =

$$\frac{\text{Moles of Maleic Anhydride Recovered}}{\text{Moles of Hydrocarbon in the Feed}} \times 100$$

$$\text{Total Conversion} = \frac{\text{Moles of Hydrocarbon Reacted}}{\text{Moles of Hydrocarbon in the Feed}} \times 100$$

$$\text{Selectivity} = \frac{\text{Single Pass Yield}}{\text{Total Conversion}} \times 100$$

EXAMPLE 24 to 27

Preparation of Maleic Anhydride From Butene-2 Using Supported Catalysts

Various catalysts were prepared using the catalyst of Example 2 having the formula $Cs_{0.5}Mo_3P_{0.33}O_x$ diluted with 30% by weight of low surface area supports (i.e. $\leq 20m^2/gram$). These catalysts were reacted with butene-2 and air in the same manner described above. The results of these experiments appear in TABLE II.

TABLE I

| | | Preparation of Maleic Anhydride from Butene-2 | | | | | | | |
| | | Hours on | Temp. °C | | Ratio, Feed | | | REsults, % | |
| Example | Catalyst | Stream | Bath | Exotherm | Air | HC | $H_2O$ | Total Acid* | Maleic Anhydride |
|---|---|---|---|---|---|---|---|---|---|
| 5 | $Rb_{0.5}Mo_3P_{0.33}Ox$ | 31.0 | 410 | 423 | 89 | 1 | 0 | 57.9 | 46.9 |
| 6 | " | 55.0 | 416 | 427 | 60 | 1 | 21 | 57.4 | 41.1 |
| 7 | " | 76.0 | 438 | 451 | 60 | 1 | 10 | 61.9 | 46.4 |
| 8 | " | 79.0 | 438 | 455 | 36 | 1 | 6 | 58.9 | 47.3 |
| 9 | " | 83.0 | 442 | 457 | 42 | 1 | 0 | 47.9 | 38.4 |
| 10 | $Cs_{0.5}Mo_3P_{0.33}Ox$ | 1.8 | 384 | 398 | 81 | 1 | 0 | 41.7 | 30.0 |
| 11 | " | 3.5 | 403 | 418 | 81 | 1 | 0 | 51.1 | 37.4 |

TABLE I-continued

| | | Preparation of Maleic Anhydride from Butene-2 | | | | | | |
|---|---|---|---|---|---|---|---|---|
| 12 | " | 19.4 | 415 | 431 | 80 | 1 | 0 | 51.4 | 36 |
| 13 | " | 334.1 | 415 | 430 | 79 | 1 | 0 | 54.1 | 37.4 |
| 14 | " | 337.0 | 421 | 440 | 79 | 1 | 0 | 56.6 | 39.6 |
| 15 | $Tl_{0.5}Mo_3P_{0.33}Ox$ | 4.0 | 325 | 342 | 74 | 1 | 0 | 35.7 | 35.7 |
| 16 | " | 5 | 339 | 359 | 74 | 1 | 0 | 43.8 | 43.8 |
| 17 | " | 25 | 353 | 372 | 72 | 1 | 0 | 44.4 | 44.4 |
| 18 | " | 27 | 363 | 386 | 69 | 1 | 0 | 46.6 | 46.6 |
| 19 | " | 29 | 377 | 402 | 69 | 1 | 0 | 48.2 | 48.2 |
| 20 | " | 46 | 386 | 413 | 69 | 1 | 0 | 51.0 | 51.0 |
| 21 | $In_{0.5}Mo_3P_{0.33}Ox$ | 3.0 | 386 | 401 | 76 | 1 | 0 | 40.6 | 40.6 |
| 22 | " | 23 | 399 | 421 | 74 | 1 | 0 | 39.5 | 39.5 |
| 23 | " | 27 | 396 | 414 | 74 | 1 | 0 | 41.7 | 41.7 |

*Measured as total acid

TABLE II

Performance of Supported Catalysts in the Preparation of Maleic Anhydride from Butene-2

| Example | Catalyst | Hours on Stream | Air/HC Ratio | Temp. °C Bath | Temp. °C Exotherm | Results, % Total Acid | Results, % Maleic Anhydride |
|---|---|---|---|---|---|---|---|
| 24 | 70% $Cs_{0.5}Mo_3P_{0.33}Ox$ + 30% $SiO_2$ | 45 | 85 | 332 | 346 | 40.1 | 18.7 |
| 25 | 70% $Cs_{0.5}Mo_3P_{0.33}Ox$ + 30% $TiO_2$ | 44 | 74 | 395 | 418 | 49.4 | 36.0 |
| 26 | 70% $Cs_{0.5}Mo_3P_{0.33}Ox$ + 30% $ZrO_2$ | 71 | 78 | 430 | 446 | 56.0 | 41.9 |
| 27 | 70% $Cs_{0.5}Mo_3P_{0.33}Ox$ + 30% $Al_2O_3$ | 3 | 84 | 383 | 396 | 41.3* | |

*Measured as total acid

We claim:

1. In the process for the production of maleic anhydride by the oxidation of n-butane, n-butenes, 1,3-butadiene or mixture thereof with molecular oxygen in the vapor phase at a reaction temperature of about 250° to 600° C in the presence of a catalyst, the improvement comprising using as a catalyst a catalyst of the formula $$X_aMo_3P_bO_x$$

wherein
X is at least one element selected from the group consisting of As, Rb, Pd, Cd, Cs, Tl and In; and wherein
$a$ is a positive number less than about 10;
$b$ is a positive number less than about 3;
$x$ is the number of oxygens required to satisfy the valence states of the other elements present.

2. The process of claim 1 wherein $a$ is a positive number less than about 7.

3. The process of claim 1 wherein $b$ is a positive number less than about 2.

4. The process of claim 1 wherein $a$ is 0.01 to 3 and $b$ is 0.01 to 1.

5. The process of claim 1 wherein X is at least one element selected from the group consisting of Rb, Cs, Tl and In.

6. The process of claim 1 wherein X is rubidium.

7. The process of claim 1 wherein X is cesium.

8. The process of claim 1 wherein X is indium.

9. The process of claim 1 wherein X is thallium.

10. The process of claim 1 wherein the active catalytic material is supported on titania, zirconia, alumina, or silica.

11. The process of claim 1 wherein n-butenes are reacted.

* * * * *

UNITED STATES PATENT AND TRADEMARK OFFICE
CERTIFICATE OF CORRECTION

PATENT NO. : 4,087,446
DATED : May 2, 1978
INVENTOR(S) : Noel J. Bremer et al

It is certified that error appears in the above-identified patent and that said Letters Patent are hereby corrected as shown below:

In Table I

Example 14, Total Acid Results Column, "56.6" should be --56.5--

Examples 15 to 23, Maleic Anhydride Results Column, all entries should be blank spaces.

Signed and Sealed this

Twentieth Day of March 1979

[SEAL]

Attest:

RUTH C. MASON
*Attesting Officer*

DONALD W. BANNER
*Commissioner of Patents and Trademarks*